United States Patent
Scherkowski

(10) Patent No.: US 11,662,749 B2
(45) Date of Patent: May 30, 2023

(54) APPARATUS AND METHOD FOR METERED DISPENSING OF A MICROFLUIDIC AMOUNT OF FLUID IN THE PICOLITER AND MICROLITER RANGE AND HAND-HELD DEVICE FOR LOCALLY PIERCING HUMAN OR ANIMAL SKIN

(71) Applicant: MT.DERM GmbH, Berlin (DE)

(72) Inventor: Dirk Scherkowski, Berlin (DE)

(73) Assignee: MT.DERM GMBH, Berlin (DE)

(*) Notice: Subject to any disclaimer, the term of this patent is extended or adjusted under 35 U.S.C. 154(b) by 363 days.

(21) Appl. No.: 17/127,386

(22) Filed: Dec. 18, 2020

(65) Prior Publication Data
US 2021/0191431 A1  Jun. 24, 2021

(30) Foreign Application Priority Data
Dec. 20, 2019 (EP) .................................... 19218747

(51) Int. Cl.
G05D 7/06 (2006.01)
A61M 37/00 (2006.01)

(52) U.S. Cl.
CPC ....... *G05D 7/0694* (2013.01); *A61M 37/0084* (2013.01)

(58) Field of Classification Search
CPC .................................................. G05D 7/0694
See application file for complete search history.

(56) References Cited

U.S. PATENT DOCUMENTS 3,754,565 A * 8/1973 Gennetten ............. B60R 25/042
137/552.5
4,168,719 A * 9/1979 Renshaw ................ F23N 1/005
137/625.5

FOREIGN PATENT DOCUMENTS

| DE | 102010017216 A1 | 12/2011 |
| EP | 2392842 A1 | 5/2013 |
| EP | 3450020 A1 | 3/2019 |
| EP | 3485974 A1 | 5/2019 |

* cited by examiner

*Primary Examiner* — Eric Keasel
(74) *Attorney, Agent, or Firm* — Leason Ellis LLP

(57) ABSTRACT

Metered dispensing of a microfluidic amount of fluid from a reservoir comprises a pressure device which applies a discharge pressure for fluid ejection via a discharge line through a valve arrangement. The valve device has a first valve with a minimum closing time and a second valve with a minimum opening time. A control device provides control signals for operation for metered dispensing of the amount of fluid as follows: a shortened minimum opening time for freeing the discharge line for the fluid flow, which time is shorter than the minimum opening time of the second valve; and a shortened minimum closing time for closing the discharge line for the fluid flow, which time is shorter than the minimum closing time of the first valve. Furthermore, a hand-held device for locally piercing human or animal skin is disclosed.

13 Claims, 3 Drawing Sheets

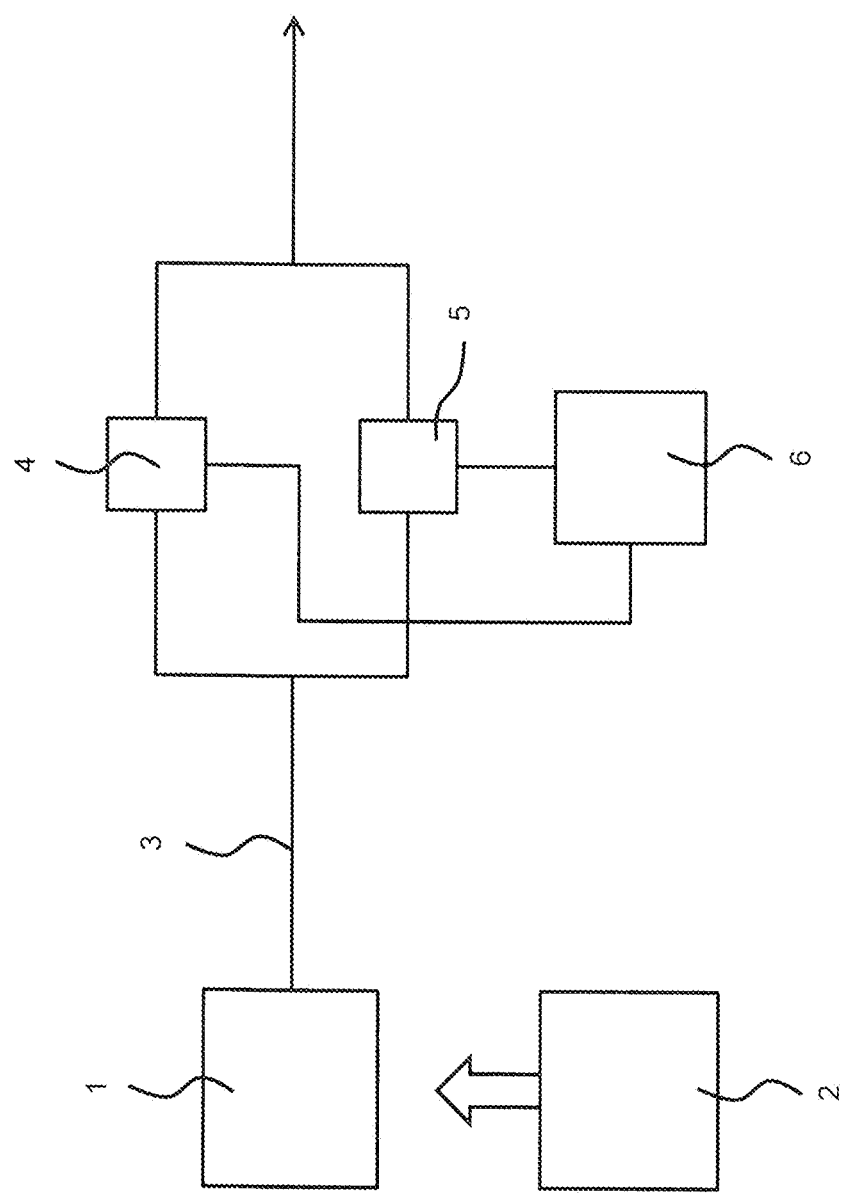

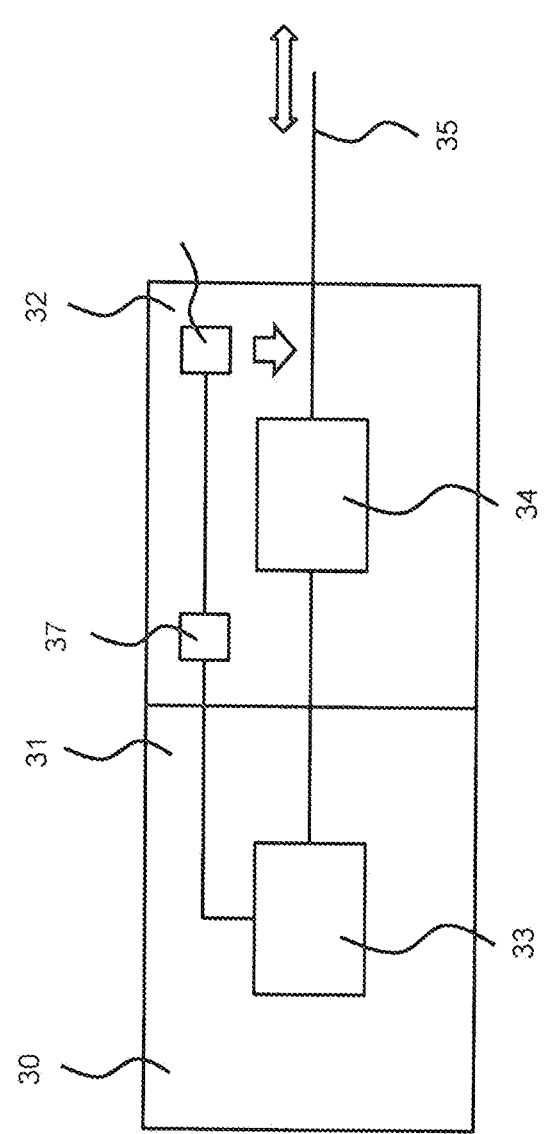

APPARATUS AND METHOD FOR METERED DISPENSING OF A MICROFLUIDIC AMOUNT OF FLUID IN THE PICOLITER AND MICROLITER RANGE AND HAND-HELD DEVICE FOR LOCALLY PIERCING HUMAN OR ANIMAL SKIN

CROSS-REFERENCE TO RELATED APPLICATIONS

The present application claims priority to European Patent Application No. 19218747.4 filed on Dec. 20, 2019, which is hereby incorporated by reference in its respective entirety.

The disclosure relates to an apparatus and to a method for metered dispensing of a microfluidic amount of fluid in the picoliter and microliter range, and to a hand-held device for locally piercing human or animal skin.

BACKGROUND

In connection with various applications, there is a need to repeatedly provide and dispense metered amounts of fluid, for example in the form of fluid pulses, from a reservoir. This is the case, for example, with hand-held appliances for locally piercing human or animal skin in connection with tattooing or the introduction of a medical or cosmetic active ingredient into the skin. With the aid of a piercing device of the hand-held appliance, the skin is pierced locally. For this purpose, a fluid amount of the substance to be introduced into the skin is to be provided in a temporally coordinated manner. However, it is often necessary to repeatedly provide metered amounts of fluid in other applications as well, for example in the field of microfluidics.

In an apparatus which has a reservoir with a fluid to be discharged, a valve can be used in a discharge line which is in communication with the fluid reservoir in order to open and close the discharge line for dispensing the fluid. Such valves usually have a valve characteristic that characterizes the behavior of the valve during operation. This includes the timing of the opening and closing of the valve. In the case of a valve in the form of an opener, the dispensing of a metered amount of fluid is limited to the minimum opening time of the valve used. Conversely, the minimum time for which the discharge line can be closed for the fluid flow is limited by the minimum closing time of a valve in the form of a closer, in which the valve is open in the rest position and closed in the working position.

Document EP 3 485 974 A1 discloses a micrometering device and a method for generating a micrometered volume of a fluid sample in the form of a micro-free jet by abruptly displacing a predetermined microvolume and a system consisting of this micrometering device and a pipetting apparatus.

Document EP 3 450 020 A1 relates to a micrometering device for generating a micrometered volume of a fluid sample in the form of a micro-free jet by abruptly displacing a predetermined microvolume.

Document DE 10 2010 017 216 A1 relates to a valve apparatus for controlling a flow of a fluid through a fluid channel with a hose made of flexible material in which a portion of a fluid channel is formed, a valve component associated with the hose, a cantilever arm which is formed on the valve component so as to be reversibly displaceable against a restoring force provided at least partially by the cantilever arm itself, a squeezing element which is arranged on a distal end of the cantilever arm for mounting the cantilever arm on the valve component and is configured to control a flow of a fluid through the fluid channel by pressing against an outer surface of the hose, optionally until the fluid channel is closed, and an actuator which is associated with the squeezing element and is configured to displace the squeezing element against the restoring force on the cantilever arm in different control positions, so that the pressure of the squeezing element on the outer surface of the hose and thus the flow through the fluid channel is adjustable.

Document EP 2 392 842 A1 relates to a valve apparatus for controlling a flow of a fluid through a fluid channel with a hose made of flexible material in which a portion of a fluid channel is formed, a valve component associated with the hose, a squeezing element which is formed on the valve component and is configured to control a flow of a fluid through the fluid channel by pressing against an outer surface of the hose, optionally until the fluid channel is closed, a guide portion which is formed on the valve component, and a guide associated with the valve component and which, during a relative movement of the guide and the valve component with respect to one another in the longitudinal direction of the hose, interacts with the guide portion in such a way that during the relative movement the squeezing element is displaced, changing the pressure on the outer surface of the hose and thus the flow through the fluid channel. Furthermore, an arrangement with at least one valve apparatus and a multi-way valve apparatus is disclosed.

SUMMARY

It is an object of the present disclosure to provide an apparatus and a method for metered dispensing of a microfluidic amount of fluid in the picoliter and microliter range and an improved hand-held device for locally piercing human or animal skin, in which the possibilities for varying the metered dispensing of an amount of fluid are expanded, in particular for shortened opening and closing of a discharge line through which the amount of fluid is discharged.

To achieve this, an apparatus and a method for metered dispensing of an amount of fluid according to independent claims 1 and 7 are provided. Furthermore, a hand-held device or apparatus for locally piercing human or animal skin according to claim 8 is provided. Embodiments are the subject matter of dependent claims.

According to one aspect, an apparatus for metered dispensing of a microfluidic amount of fluid in the picoliter and microliter range is provided, which comprises the following: a reservoir configured to hold or receive a fluid; a discharge line or channel which is in fluid communication with the reservoir and through which an amount of the fluid can be discharged from the reservoir; and a pressure device which is set up to apply a discharge pressure to the fluid in such a way that the amounts of fluid are ejected via the discharge line. Furthermore, the apparatus has a valve device with a first valve in the form of a closer in the discharge line, which first valve is open in a rest position in order to free the discharge line for a fluid flow and is closed in a working position in order to close the discharge line for a fluid flow, wherein the first valve has a minimum closing time as a valve characteristic. The valve device also has a second valve in the form of an opener in the discharge line, which second valve is closed in the rest position in order to close the discharge line for the fluid flow and is open in a working position in order to free the discharge line for the fluid flow, wherein the second valve has a minimum closing time as a valve characteristic. In the apparatus, a control device is provided which is connected to the first and the second valves and is set up to provide first control signals for actuating the first valve and second control signals for actuating the second valve, in such a way that, by actuating the first and the second valves for the discharge line, at least one of the following modes of operation for metered dispensing of the amount of fluid can be carried out: a shortened minimum opening time for freeing the discharge line for the fluid flow, which time is shorter than the minimum opening time of the second valve, and a shortened minimum closing time for closing the discharge line for the fluid flow, which time is shorter than the minimum closing time of the first valve.

According to a further aspect, a method for the metered dispensing of a microfluidic amount of fluid in the picoliter and microliter range is provided, with the following steps: providing a fluid to be dispensed in a reservoir; a discharge line which is in fluid communication with the reservoir and through which an amount of the fluid can be discharged from the reservoir; applying a discharge pressure to the fluid by means of a pressure device, in such a way that the amount of fluid is ejected via the discharge line; and controlling the ejection of the amount of fluid by means of a valve device and a control device connected thereto. The valve device has the following: a first valve in the form of a closer in the discharge line, which first valve is open in a rest position in order to free the discharge line for a fluid flow, and is closed in a working position in order to close the discharge line for a fluid flow, the first valve having a minimum closing time as a valve characteristic; and a second valve in the form of an opener in the discharge line, which second valve is closed in a rest position in order to close the discharge line for the fluid flow and is open in a working position in order to free the discharge line for the fluid flow, the second valve having a minimum opening time as a valve characteristic. The control device provides first control signals for actuating the first valve and second control signals for actuating the second valve in such a way that, by actuating the first and the second valves for the discharge line, at least one of the following modes of operation for metered dispensing of the amount of fluid can be carried out: a shortened minimum opening time for freeing the discharge line for the fluid flow, which time is shorter than the minimum opening time of the second valve; and a shortened minimum closing time for closing the discharge line for the fluid flow, which time is shorter than the minimum closing time of the first valve.

According to a further aspect, a hand-held device is provided for locally piercing human or animal skin with such an apparatus for metered dispensing of a microfluidic amount of fluid in the picoliter and microliter range. For example, it may be a hand-held appliance for tattooing or for permanent makeup.

The combination of the first and the second valves in the form of a closer/opener in the discharge line makes it possible to control the discharge of the metered amount of fluid, for example in the form of fluid pulses, by actuating both valves. Both the valve in the form of a closer and also the valve in the form of an opener are arranged in the discharge line and can open and close the discharge line, respectively. This improves the variability for controlling the opening and closing of the discharge line in comparison to the provision of one single valve arranged in the discharge line with a fixed valve characteristic. The combination of the valves enables an improved adaptation of the modes of operation to different applications for metered dispensing of the amount of fluid. A shortened minimum opening time and/or a shortened minimum closing time are provided. This makes it possible to provide shortened opening/closing times for the discharge line in comparison to the known operation with only one valve, in the form of a closer or opener, and therefore shortened fluid pulses are made possible.

It is thus possible to provide and dispense microfluidic amounts of the fluid in the picoliter and microliter range (field of microfluidics). If desired, larger amounts of fluid can also be dispensed with the aid of the arrangement of valves, in particular by simply increasing the opening time so that larger amounts of fluid are dispensed, for example up to milliliters. However, the proposed technology makes it possible, in particular, to meter the microfluidic amounts of the fluid, optionally also repeatedly one after the other.

In addition to the combination of the first and the second valves, one or more further valves can be arranged in the discharge line. The actuation of the one or more further valves for opening and closing can be carried out in a coordinated manner by the control device in combination with the first and the second valves.

Either the first or the second valve may be arranged closest to the pressure device in the discharge line.

In one embodiment, the pressure device may be formed such that the discharge pressure (static pressure) is applied to the amount of fluid solely under the effect of the force of gravity acting on it.

Furthermore, the control device may be configured to provide the first control signals for actuating the first valve and the second control signals for actuating the second valve in such a way that the shortened minimum opening time for freeing the discharge line for the fluid flow is shorter than the minimum closing time of the first valve. In this embodiment, the shortened minimum opening time is both shorter than the minimum opening time of the second valve and also shorter than the minimum closing time of the first valve.

The control device may be configured p to provide the first control signals for actuating the first valve and the second control signals for actuating the second valve in such a way that the shortened minimum closing time for closing the discharge line for the fluid flow is shorter than the minimum opening time of the second valve. In this embodiment, the shortened minimum closing time for closing the discharge line is both shorter than the minimum closing time of the first valve and also shorter than the minimum opening time of the second valve.

The first and the second control signals may be configured or set up to provide at least one of the following modes of operation with a repetition frequency: repeated opening of the discharge line for the fluid flow with the shortened minimum opening time, and repeated closing of the discharge line for the fluid flow with the shortened minimum closing time. In this embodiment, fluid pulses or fluid amounts in a pulsed mode of operation are provided and dispensed at the repetition frequency. The repetition frequency can be, for example, approximately 0.1 Hz to approximately 100 Hz, alternatively approximately 0.1 Hz to approximately 15 Hz.

The first valve and the second valve may be arranged in the discharge line according to a series connection of valves. A series connection is suitable for dispensing extremely precisely metered, smallest amounts of fluid, for example at a high repetition rate.

The first valve and the second valve may be arranged in the discharge line according to a parallel connection of valves. The parallel connection is suitable for generating particularly short interruptions to metering in an otherwise continuous fluid flow and thus for delivering precisely metered fluid with smallest interruptions with the highest repetition precision and at a high repetition rate.

The first and the second valves may be arranged in a common valve housing. In particular, the arrangement may be designed in such a way that a common fluid control part is formed, on which both an opener actuator and a closer actuator act.

The proposed technology may be used, for example, for the construction of a so-called fluid circuit board in lab-on-a-chip concepts and/or for a switching element in fluid computers.

The hand-held appliance may have a drive module and a piercing module coupled releasably or non-releasably thereto. With the aid of a drive device in the drive module, a non-manually (mechanically) produced drive force or drive movement is provided for a piercing device arranged in the piercing module, for example using an electric motor. The piercing module can be a disposable module. Various embodiments are known per se for such hand-held appliances for locally piercing skin.

Alternatively, a manually actuatable piercing device can be provided. In order to control the dispensing or metering of the amount of fluid in a manner coordinated with the manually triggered piercing movement, the piercing movement is detected by means of a sensor device. For example, a sensor device can be provided by means of which a movement of a piercing needle is detected. Alternatively or in addition, a tilt sensor can detect a tilting movement that indicates the piercing movement. Based on this the microfluidic amount of fluid is then metered, in particular by actuating the metering device.

In one embodiment, an apparatus for injecting or applying a substance into human or animal skin can thus be formed. The apparatus can be set up for lab-on-chip applications or fluid metering in the field of medical analysis devices. An embodiment for valve union/fusion can be provided, in particular in connection with miniature valves.

The possibility provided by means of the proposed technology to meter a fluid, accurately repeatably and repeatedly, in precisely metered amounts, in particular amounts of fluid in the microliter to picoliter range, can be used in applications, for example, in the field of subminiature valves. The apparatus for metered dispensing of the amount of fluid is then designed as a sub-miniature valve. Such sub-miniature valves can be constructed with an actuator made of so-called shape memory alloys (SMA), for example with actuator parts made from just one wire component or foil component. After appropriate pretreatment and choice of alloy, these parts change their shape as required when heated, for example transitioning from a first shape to a second shape. Such heating can be obtained, for example, by means of an electrical current flow which is impressed on the metallic SMA material as an electrical control signal and is implemented via the power loss at the electrical resistance of the material. When the electrical control current is interrupted, the actuator part cools down again and assumes its first shape. With the aid of a controlled, stronger current signal, the heating and thus the shape transition in the direction from the rest position to the working position, i.e. in the example from the first shape to the second shape, can be forced in order to obtain a short rise time, but the opposite transition then takes place passively and significantly more slowly via cooling processes, which disadvantageously increases the fall time. Typical subminiature valve switching times can, for example, be symmetrically in the range from approximately 60 ms to approximately 80 ms for opening and closing, forced at approximately 10 ms in a first direction, wherein the return to the starting position can then take, for example, approximately 120 ms or longer.

In one embodiment, in the apparatus for metered dispensing of the fluid the first and the second valves are constructed as a valve with an actuator made of a shape memory alloy, in particular a sub-miniature valve.

The embodiments explained above in connection with the microfluidic apparatus for metered dispensing of the microfluidic amount of fluid can be provided correspondingly in connection with the microfluidic method for metered dispensing and/or the hand-held appliance.

DESCRIPTION OF EMBODIMENTS

Further embodiments are explained in greater detail below with reference to the drawings, in which:

FIG. 2 is a schematic representation of an arrangement for an apparatus for metered dispensing of a microfluidic amount of fluid, in which a first and a second valve are arranged in a parallel connection in the discharge line; and FIG. 3 is a schematic representation of an arrangement for a hand-held appliance for locally piercing human or animal skin.

Figure 1:
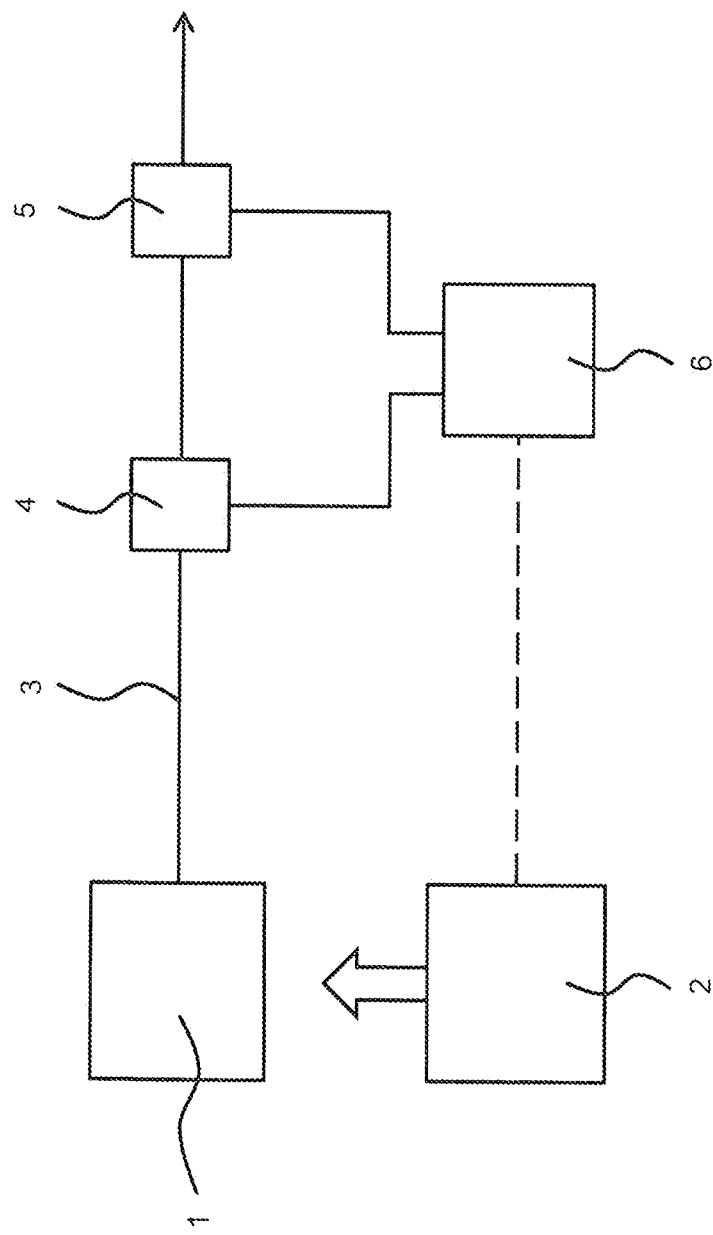
FIG. 1 is a schematic representation of an arrangement for an apparatus for metered dispensing of a microfluidic amount of a fluid, in which a first and a second valve are arranged in a series connection in a discharge line.

FIG. 1 is a schematic representation of an arrangement for an apparatus for metered dispensing or metering of a microfluidic amount of fluid, in the context of single-pulse dispensing or repeated dispensing of metered amounts of fluid with a (variable) repetition frequency. An amount of a fluid to be dispensed, for example a cosmetic or medical active substance or a dye, is held in a fluid reservoir 1. In principle, any fluids, in particular liquids, can be held in the fluid reservoir 1 in order to dispense them in a metered manner.

A pressure device 2 is provided, by means of which pressure is applied to the fluid to be dispensed so that the fluid can be ejected in a metered manner through a discharge line 3 which connects to the fluid reservoir 1. For example, the pressure device 2 has a pump.

In the discharge line 3, a first valve 4 and a second valve 5 are arranged one behind the other, corresponding to a series connection. The first valve 4 is in the form of a closer, which is open in a rest or starting (valve) position in order to free the discharge line 3 for a fluid flow and is closed in a working (valve) position in order to close the discharge line 3 for the fluid flow. The second valve 5 is in the form of an opener, which is closed in a rest position in order to close the discharge line 3 for the fluid flow, and in a working position is open in order to free the discharge line 3 for the fluid flow. The first valve 4 is equipped with a minimum closing time corresponding to a valve characteristic. The second valve 5 is designed with a minimum opening time corresponding to its valve characteristic.

A control device 6 is provided which is connected to the first and the second valves 4, 5. Optionally, the control device 6 can also be connected to the pressure device 2 in order to control the operation thereof, for example for a time-coordinated application of pressure for valve actuation.

With the aid of the control device 6, first control signals for actuating the first valve 4 and second control signals for actuating the second valve 5 are provided. With the aid of the first and the second control signals, the first and the second valves 4, 5 are opened and closed in a controlled manner during operation. The first and the second control signals can be provided by the control device 6 in such a way that one or more modes of operation are implemented for metered dispensing of an amount of fluid through the discharge line 3. This includes opening the discharge line 3 for a shortened minimum opening time in order to free the discharge line 3 for the fluid flow, wherein the shortened minimum opening time is shorter than the minimum opening time of the second valve 5 and optionally also shorter than the minimum closing time of the first valve 4. By actuating the first and second valve 4, 5 it is thus possible to eject or dispense shorter fluid pulses in terms of time than would be possible by actuating only the second valve 5 in the form of an opener. As an alternative or in addition, a mode of operation can be provided in which the discharge line is closed by actuating the first and second valves 4, 5 for a shortened minimum closing time which is shorter than the minimum closing time of the first valve 4.

FIG. 2 shows a schematic representation of a further arrangement for an apparatus for metered dispensing of an amount of fluid, in which the first and second valves 4, 5, in contrast to the embodiment in FIG. 1, are now arranged in a parallel connection. With regard to the generation of the first and the second control signals by means of the control device 6 as well as the modes of operation for the discharge line 3 which can be implemented thereby, the explanations given above in connection with the embodiment in FIG. 1 apply mutatis mutandis. The actuation of the first and second valve 4, 5 coordinated and synchronized by means of the control device 6 enables variable opening and closing of the discharge line 3, wherein in particular a shortened opening/closing of the discharge line 3 can be provided in comparison to the minimum closing/opening time of the individual valves.

The arrangements explained above and with reference to FIGS. 1 and 2 can be used, for example, in a hand-held appliance for locally piercing human or animal skin, in order to provide metered fluid amounts of a substance to be introduced into the skin in the case of such a piercing appliance.

FIG. 3 is a schematic representation of an arrangement for such a hand-held appliance 30. The hand-held appliance 30 has a drive module 31 and a piercing module 32 coupled releasably or non-releasably thereto. With the aid of a drive device 33 in the drive module 31, a non-manually (mechanically) generated drive force or drive movement is provided for a piercing device 34 arranged in the piercing module 32, for example using an electric motor. The piercing module 32 can be a disposable module. Various embodiments are known per se for such hand-held appliances for locally piercing skin.

With the aid of the driving force, a piercing needle 35 of the piercing device 34, which can be formed with a single needle or a group of needles, is extended and retracted in a single piercing mode or repeatedly according to a repetition frequency. In this way, human or animal skin can be pierced locally. A metered amount of fluid is provided with the aid of a metering device 36, temporally coordinated with the piercing movement, in order to, for example, provide a cosmetic or medical active ingredient which can be introduced via the pierced skin. The metering device 36 comprises an arrangement in the embodiment according to FIG. 1 or FIG. 2. The metering device 36 and also the piercing movement can be controlled, in particular coordinated with respect to time, by means of a control device 37 of the hand-held appliance 30.

Alternatively, a manually actuatable piercing device can be provided. In order to control the dispensing or metering of the amount of fluid in a manner coordinated with the manually triggered piercing movement, the piercing movement is detected by means of a sensor device. Based on this, the microfluidic amount of the fluid is then metered, in particular by actuating the metering device 36.

The features disclosed in the above description, the claims and the drawings may be relevant to implementing the different embodiments both individually and also in any combination.

The invention claimed is:

1. An apparatus for metered dispensing of a microfluidic amount of fluid in the picoliter and microliter range, comprising:
   a reservoir configured to receive a fluid;
   a discharge line which is in fluid communication with the reservoir and through which an amount of the fluid can be discharged from the reservoir in a metered manner;
   a pressure device which is set up to apply a discharge pressure to the fluid in such a way that the amounts of fluid are ejected via the discharge line;
   a valve device having
      a first valve in the form of a closer in the discharge line, which first valve is open in a rest position in order to free the discharge line for the fluid flow, and is closed in a working position in order to close the discharge line for a fluid flow, wherein the first valve has a minimum closing time as a valve characteristic; and
      a second valve being an opener in the discharge line, which valve is closed in a rest position in order to close the discharge line for the fluid flow, and is open in a working position in order to free the discharge line for the fluid flow, wherein the second valve has a minimum opening time as a valve characteristic; and
   a control device which is connected to the first and the second valves and is set up to provide first control signals for actuating the first valve and second control signals for actuating the second valve, in such a way that, by actuating the first and the second valves for the discharge line, at least one of the following modes of operation for metered dispensing of the amount of fluid can be carried out:
      a shortened minimum opening time for freeing the discharge line for the fluid flow, which time is shorter than the minimum opening time of the second valve; and
      a shortened minimum closing time for closing the discharge line for the fluid flow, which time is shorter than the minimum closing time of the first valve.

2. The apparatus according to claim 1, wherein the control device is also set up to provide the first control signals for actuating the first valve and the second control signals for actuating the second valve in such a way that the shortened minimum opening time for freeing the discharge line for the fluid flow is shorter than the minimum closing time of the first valve.

3. The apparatus according to claim 1, wherein the control device is also set up to provide the first control signals for actuating the first valve and the second control signals for actuating the second valve in such a way that the shortened minimum closing time for closing the discharge line for the fluid flow is shorter than the minimum closing time of the second valve.

4. The apparatus according to claim 1, wherein the first and the second control signals are configured to provide at least one of the following modes of operation with a repetition frequency:

repeated opening of the discharge line for the fluid flow with the shortened minimum opening time; and repeated closing of the discharge line for the fluid flow with the shortened minimum closing time.

5. The apparatus according to claim 1, wherein the first valve and the second valve are arranged in the discharge line according to a series connection of valves.

6. The apparatus according to claim 1, wherein the first valve and the second valve are arranged in the discharge line according to a parallel connection of valves.

7. A method for metered dispensing of a microfluidic amount of fluid in the picoliter and microliter range, comprising:

providing a fluid to be dispensed in a reservoir;

providing a discharge line which is in fluid communication with the reservoir and through which an amount of the fluid can be discharged from the reservoir in a metered manner;

applying a discharge pressure to the fluid by means of a pressure device in such a way that the amount of fluid is ejected via the discharge line; and controlling the ejection of the amount of fluid by means of a valve device and a control device connected thereto, the valve device comprising a first valve in the form of a closer in the discharge line, which first valve is open in a rest position in order to free the discharge line for a fluid flow, and is closed in a working position in order to close the discharge line for a fluid flow, wherein the first valve has a minimum closing time as a valve characteristic; and a second valve in the form of an opener in the discharge line, which is closed in a rest position in order to close the discharge line for the fluid flow, and is open in a working position in order to free the discharge line for the fluid flow, wherein the second valve has a minimum opening time as a valve characteristic;

wherein the control device provides first control signals for actuating the first valve and second control signals for actuating the second valve in such a way that, by actuating the first and the second valves for the discharge line, at least one of the following modes of operation for metered dispensing of the amount of fluid is carried out:

a shortened minimum opening time for freeing the discharge line for the fluid flow, which time is shorter than the minimum opening time of the second valve; and a shortened minimum closing time for closing the discharge line for the fluid flow, which time is shorter than the minimum closing time of the first valve.

8. A hand-held device for locally piercing human or animal skin, with an apparatus for metered dispensing of a microfluidic amount of fluid in the picoliter and microliter range, the hand-held device comprising:

a reservoir configured to receive a fluid;

a discharge line which is in fluid communication with the reservoir and through which an amount of the fluid can be discharged from the reservoir in a metered manner;

a pressure device which is set up to apply a discharge pressure to the fluid in such a way that the amounts of fluid are ejected via the discharge line;

a valve device having a first valve in the form of a closer in the discharge line, which first valve is open in a rest position in order to free the discharge line for the fluid flow, and is closed in a working position in order to close the discharge line for a fluid flow, wherein the first valve has a minimum closing time as a valve characteristic; and a second valve being an opener in the discharge line, which valve is closed in a rest position in order to close the discharge line for the fluid flow, and is open in a working position in order to free the discharge line for the fluid flow, wherein the second valve has a minimum opening time as a valve characteristic; and a control device which is connected to the first and the second valves and is set up to provide first control signals for actuating the first valve and second control signals for actuating the second valve, in such a way that, by actuating the first and the second valves for the discharge line, at least one of the following modes of operation for metered dispensing of the amount of fluid can be carried out:

a shortened minimum opening time for freeing the discharge line for the fluid flow, which time is shorter than the minimum opening time of the second valve; and a shortened minimum closing time for closing the discharge line for the fluid flow, which time is shorter than the minimum closing time of the first valve.

9. The hand-held device according to claim 8, wherein the control device is also set up to provide the first control signals for actuating the first valve and the second control signals for actuating the second valve in such a way that the shortened minimum opening time for freeing the discharge line for the fluid flow is shorter than the minimum closing time of the first valve.

10. The hand-held device according to claim 8, wherein the control device is also set up to provide the first control signals for actuating the first valve and the second control signals for actuating the second valve in such a way that the shortened minimum closing time for closing the discharge line for the fluid flow is shorter than the minimum closing time of the second valve.

11. The hand-held device according to claim 8, wherein the first and the second control signals are configured to provide at least one of the following modes of operation with a repetition frequency:

repeated opening of the discharge line for the fluid flow with the shortened minimum opening time; and repeated closing of the discharge line for the fluid flow with the shortened minimum closing time.

12. The hand-held device according to claim 8, wherein the first valve and the second valve are arranged in the discharge line according to a series connection of valves.

13. The hand-held device according to claim 8, wherein the first valve and the second valve are arranged in the discharge line according to a parallel connection of valves.

* * * * *